United States Patent [19]
Morrison

[11] Patent Number: 5,869,238
[45] Date of Patent: Feb. 9, 1999

[54] QUANTITATIVE METHOD OF MEASURING METASTATIC ACTIVITY

[75] Inventor: Dennis R. Morrison, Kemah, Tex.

[73] Assignee: The United States of America as represented by the Administrator of the National Aeronautics and Space Administration, Washington, D.C.

[21] Appl. No.: 390,904

[22] Filed: Feb. 16, 1995

Related U.S. Application Data

[63] Continuation of Ser. No. 97,186, Jul. 27, 1993, abandoned.
[51] Int. Cl.$^6$ .......................... C12Q 1/68; G01N 33/574; G01N 33/48
[52] U.S. Cl. .................................. 435/6; 435/7.23; 436/64
[58] Field of Search ................................ 435/7.23, 6, 15, 435/973, 968; 436/800, 805, 64

[56] References Cited

U.S. PATENT DOCUMENTS

| | | | |
|---|---|---|---|
| 4,276,375 | 6/1981 | Claeson et al. | 435/13 |
| 4,668,618 | 5/1987 | Thornthwaite | 435/6 |
| 4,741,043 | 4/1988 | Bacus | 382/6 |
| 4,752,583 | 6/1988 | Jensen et al. | 435/240.27 |
| 4,780,406 | 10/1988 | Dolbeare et al. | 435/6 |
| 4,808,528 | 2/1989 | Tryggvason et al. | 435/172.2 |

OTHER PUBLICATIONS

Suzuki et al. "An introduction to Genetic analysis." Foruth Ed. Freeman and Co., NY. pp. 207–212 and 722, 1989.
Merkel, D.E., Therapy of Breast Cancer, Genoa, Italy, Meeting Abstract, Sep. 1989.
Hollas, W. et al, Cancer Research, vol. 51, pp. 3690–3695, Jul. 1991.
Rao, J.Y. et al, Cancer Research, vol. 50, pp. 2215–2220, Apr. 1990.
Spyratos, F. et al., Proc. Annu. Meet. Am. Cancer Res., vol. 33, A1579, 1992.
Spyratos, F. et al., J. of the Nat. Cancer Inst., vol. 84, No. 16, pp. 1266–1272, Aug. 1992.
"Plasminogen Activator Content Of Gynecological Tumors And Their Metastases", Gynecologic Oncology 26: 364–373, S.M. Camiolo, G. Markus, & M. S. Piver, 1987.
"Comparative Study Of Plasminogen Activators In Cancers And Normal Mucosae Of Human Urinary Bladder", Cancer Research 49: 1067–1070, Y. Hasui et al, Feb. 15, 1989.
"Secretion Of Plasminogen Activators By Human Colorectal And Gastric Tumor Explants", Clin. Expl. Metastasis 6: 431–450, S. R. Harvey et al, 1988.
"Urokinase–type Plasminogen Activator (u–PA) Antigen is a Predictor of Early Relapse in Breast Cancer," Fibrinolysis 4: 69–78, F. Janicke et al, 1990.
"Tumour–Associated Fibrinolysis: The Prognostic Relevance Of Plasminogen Activators uPA and tPA in Human Breast Cancer", Blood Coagulation and Fibrinolysis 1: 695–702, 1990.
"Plasminogen Activator Secretion of Human Tumors in Short–Term Organ Culture, Including a Comparison of Primary and Metastatic Colon Tumors", Cancer Research 43: 5517–5525, G. Markus et al, 1983.
"Receptor–Medicated Internalization and Degradation of Urokinase is Caused by Its Specific Inhibitor PAI–1", EMBO Journal 9: 1079–1085, M.V. Cubellis, T. Wun, & F. Blasi, 1990.
"Flow Cytometry, Cellular DNA Content and Prognosis in Human Malignancy", J. Clin. Ocnology 5: 1690–1703, D. E. Merkel, L. G. Dressler and W. L. McGuire, 1987.
"An Immunofluorescence Method for Monitoring DNA Synthesis by Flow Cytometry", Cytometry 6: 385–389, H. G. Gratzner and R. C. Leif, 1981.
"Urokinase–Plasminogen Activator, a New and Independent Prognostic Marker in Breast Cancer", Cancer Research 50, pp. 6827–6829, Michael J. Duffy et al, 1990.
"Flow Cytometry", Arch Pathol Lab Med, vol. 107, pp. 1–6, Raul C. Braylan, MD, 1983.
"Measuring the Metastatic Potential of Cancer Cells", Technology 2002, Dennis R. Morrison et al, 2 pages, Balitmore, MD, Dec. 1992.

Primary Examiner—Sheela Huff
Assistant Examiner—Yvonne Eyler
Attorney, Agent, or Firm—James M. Cate

[57] ABSTRACT

The metastatic potential of tumors can be evaluated by the quantitative detection of urokinase and DNA. The cell sample selected for examination is analyzed for the presence of high levels of urokinase and abnormal DNA using analytical flow cytometry and digital image analysis. Other factors such as membrane associated urokinase, increased DNA synthesis rates and certain receptors can be used in the method for detection of potentially invasive tumors.

21 Claims, 2 Drawing Sheets

QUANTITATIVE METHOD OF MEASURING METASTATIC ACTIVITY

This application is a continuation of application Ser. No. 08/097,186, filed Jul. 27, 1993, now abandoned.

ORIGIN OF THE INVENTION

The invention described herein was made by an employee of the United States Government and may be manufactured and used by or for the Government of the United States of America for governmental purposes without the payment of any royalties thereof or therefor.

BACKGROUND OF THE INVENTION

Tumor cells of some cancers secrete enzymes that break down the intracellular matrix and invade adjacent tissues. The production of serine protease enzymes such as plasminogen activator enzymes have been observed in connection with the metastasis of tumor cells into healthy tissues. Plasminogen activator, enzymes have been linked to cancer detection, using assays of enzymes extracted from the tumor cells (Camiolo, S. M., Markus, G. and Piver, M. S. "Plasminogen activator content of gynecological tumors and their metastases." *Gynecolocical Oncology* 26: 364–373, 1987) or assays of supernatants from tissue culture of the tumor cells. (Hasui, Y. et al., "Comparative study of plasminogen activators in cancers and normal mucosa of human urinary bladder." *Cancer Research* 49: 1067–1070, 1989. Harvey, S. R., et al., "Secretion of plasminogen activators by human colorectal and gastric tumor explants." *Clin. Expl. Metastasis* 6: 431–450, 1988.)

Urokinase-type plasminogen activator (urokinase or uPA), a serine protease, is not produced in most normal cells, except at low levels in certain types of normal kidney cells, colon and gastric mucosa, and endothelial cells lining small arteries. Urokinase (uPA) can be present in the tissues in several molecular forms,. The inactive proenzyme (scuPA) is composed of 411 amino acids. ScuPa is converted to the active enzyme by cleavage at Lys.158–Ile.159, loss of the Lys.158 and formation of the double chain, high molecular weight form (HMW-uPA) that is 54 kDaltons. A low molecular weight form (LMW-uPA) can also be formed by cleavage of the HMW-uPA at Lys.135–Lys.136 giving a 33 KDa active enzyme.

The active urokinase enzymes convert plasminogen into plasmin, which in turn, dissolves intravascular fibrin blood clots and intracellular fibrin matrix components as well as activating collagenases, laminases, and other related enzymes which are important to the anchorage and growth regulation of cells. Urokinase is produced in a number of tumors such as lung, colon, gastric, uterine, breast, brain cancer and malignant melanoma. High levels of urokinase (>3.5 ug/mg of total protein) extracted from breast tumor tissues is an indicator for high risk of recurrence and shorter patient survival times. Janicke, et al. *Fibrinolysis* 4:69–78, 1990. Data from these clinical studies showing that a) measurements of uPA in plasma are of no value and that b) measurements of uPA in cytosol fractions give some prognostic value (0.12 benign vs. 1.65 ng/ml in metastatic breast cancer) and c) measurements of the uPA extracted from all of the tumor cells by Triton-X 100 treatment have even more significance (0.23 vs. 3.21±2.40 ng/mg of metastatic breast cancer). However, the standard deviation (S.D.) of these measurements represents ±65% for benign breast cancer and ±75% for metastatic tissues. Clearly, cell extractions cannot make the precise distinctions that are necessary as to the presence or absence of uPA, since the extractions are from tissues containing some normal cells, some cancer cells that may have no (or very little) uPA and those that may have significant amounts of uPA. (Schmidt, M. et al, "Tumour-associated fibrinolysis: the prognostic relevance of plasminogen activators uPA and tPA in human breast cancer." *Blood Coagulation and Fibrinolysis* 1: 695–072, 1990). Also cells from primary lung and colon tumor produce more uPA than cells from metastatic tumors, but different methods of extraction and assays give widely variable results (Markus, G. et al., "Plasminogen activator secretion of human tumors in short-term organ culture, including a comparison of primary and metastatic colon tumors." *Cancer Research* 43: 55-7-5525, 1983.).

It recently has been shown in cancer cells that the HMW active form of urokinase, bound to the tumor cell membrane, is responsible for the local lysis of the extracellular matrix, hence the tissue invasion mechanism for metastasis. (Hollas, W., Blasi, F., and Boyd, D. "Role of urokinase receptor in facilitating extracellular matrix invasion by cultured colon cancer." *Cancer Research* 51: 3690–3695, 1991.). The unbound uPA and the LMW form is not responsible for local dissolution of extracellular matrix in the immediate vicinity of the metastatic tumor cell. (Cubellis, M. V., Wun, T. and Blasi, F. "Receptor-mediated internalization and degradation of urokinase is caused by its specific inhibitor PAI-1." *EMBO Journal* 9: 1079–1085, 1990.). Thus the direct measurement of membrane-bound urokinase is more important to the prognostic accuracy than is measurement of all urokinase (membrane-bound and free uPA) present in cells or in the tissue specimen.

Total urokinase has been measured from tumor tissue and secretion by cultured explants. These are difficult to quantitate from biopsy to biopsy, especially if the measurements are made on a large group of cells. The data obtained is an average value of all normal and cancer cells, rather than a measurement of each individual cell. However, direct measurements of intracellular and extracellular urokinase have not been made previously.

A DNA content histogram of normal cells shows a single diploid peak (at $G_1$ phase) and a tetraploid peak (at G2+M phase). In most tumors, abnormal DNA content of tumor cells is detected as a second $G_1$ peak or multiple peaks. Abnormal DNA (DNA aneuploidy) is considered as an independent indicator of tumor aggressiveness and poor prognosis that is used to supplement cytopathology grading. Flow cytometry can be used to measure total DNA content as shown in U.S. Pat. No. 4,780,406, Dolbeare et al. entitled Flow Cytometric Measurement of Total DNA and Incorporated Halodeoxyuridine issued Oct. 25, 1988, which is incorporated herein by reference. Cells disassociated and prepared for flow cytometry can be analyzed for cell cycle stage as well as DNA content simultaneously. Flow cytometer measurement of the percentage of proliferating tumor synthesizing DNA (S-phase cells) is. an independent indicator of malignancy. High percentages (15–20%) of S-phase tumor cells usually indicates an aggressive malignancy and usually correlates well with abnormally high DNA content. The labeling index (LI) obtained by pulse-labeling cells with DNA precursors represents the rate that DNA is being synthesized in tumor cells. Usually, a LI>4% is associated with a higher probability of recurrent malignancy. (Merkel, D. E. Dressler, L. G. and McGuire, W. L., "Flow cytometry, cellular DNA content and prognosis in human malignancy." *J. Clin. Oncology* 5: 1690–1703, 1987.)

SUMMARY OF THE INVENTION

A method has been developed for quantitative detection of urokinase and correlating the urokinase levels to the DNA content and additionally to the DNA synthesis rate for evaluation of metastatic potential of tumor cells. First, the cells to be examined and evaluated are selected. The cells can be obtained from known tumor cell lines cultured for research purposes, from tumor biopsies or cytological samples from patients or any other source of tissue to be examined for metastatic activity of tumor cells. The cell sample preparations are incubated with antibodies specific to urokinase in order to directly measure its presence in the isolated cells on a cell by cell basis. The sample of cells may be prepared in suspension for analysis by analytical cytometry techniques such as flow cytometry, digital image analysis or sectioned and prepared as histology slides for digital image analysis. The intranuclear DNA also is labeled or stained (using labels or staining including propidium iodide, 4,6-diamidine-2-phenylindole, Hoechst 33258 and others known to those skilled in the art) to allow quantitative measurements of DNA content. Viable cells also can be pulse-labeled with DNA precursors, BdUr, or IdUr for a specific uptake period, then incubated with fluorescent-labeled antibodies against the precursor to quantitatively measure the DNA synthesis rates in those cells. Measurements of DNA and urokinase also are made on the same cells. DNA and urokinase measurements, may be made essentially simultaneously if flow cytometry is used, or sequentially from the same source cell population.

The cells or histology sections are incubated with antibodies or anti-antibodies specific for urokinase. Antibodies or anti-antibodies to specific forms of urokinase may also be used. The antibodies can be monoclonal or polyclonal antibodies that bind specifically to urokinase. Further, intracellular urokinase is measured as well as extracellular urokinase which is outside or associated with the cell membrane outer surface.

The antibodies specific to urokinase may be labeled with a fluorescent marker detectable by analytical cytometry techniques. Also DNA content and synthesis rate based on DNA stains or pulse-labeled uptake of DNA precursors is measured by image analysis and flow cytometry. The same cell sample can be measured for DNA content and urokinase by vital staining the DNA and labeling the urokinase with a marker so that both the DNA and urokinase can be measured simultaneously using two-color image analysis or flow cytometry.

The presence of urokinase, particularly the inactive proenzyme scuPA and the high molecular weight form H, is correlated to DNA content to determine if the profile of the urokinase to DNA ratio is within a range indicating metastatic activity. The cells are measured individually on a cell by cell basis so that the population examined can be ranked to determine whether a high percentage of the cells have high urokinase and abnormal DNA levels that indicates metastatic activity. Relatively high urokinase and abnormal DNA will indicate the need for aggressive oncology, radiation or immunologic cancer therapy and adjuvant treatment following surgical excision of the tumor.

In addition to urokinase and DNA content, other factors for evaluating metastatic potential can be used with the method of this invention. DNA synthesis rates indicating aggressive tumor growth can be measured as described above and correlated with cell surface receptors for tumor growth factors such as EGF and hormones such as estrogen and progesterone. Also, other antibody specific markers that may be helpful in indicating the stage of tumor development may be used in conjunction with this method. For instance a quantitative measurement for plasminogen activator inhibitor, urokinase receptor and other associated hormone receptors have been made with the urokinase measurements.

By establishing a correlation between urokinase and DNA content and labeling for DNA synthesis rate a screening process can be used to identify metastatic tumor cells. The isolated tissue is examined for cells containing urokinase. Initial urokinase measurements may be made directly with fluorescent labeled antibodies or indirectly with anti-uPa antibodies and fluorescent secondary antibodies or by assays for enzyme activity or by other biochemical means. Cells without a significant amount of urokinase need not be examined further. For samples with cells with higher than normal urokinase, then DNA content is measured. If the urokinase levels are high in cells with abnormal DNA content, the direct measurement of extracellular, especially membrane-bound, and intracellular urokinase content can be made. The correlation between abnormal DNA content and extracellular urokinase would then be made. Cells or populations of cells that do not meet the initial screening criteria for metastatic potential do not have to undergo the more intensive steps of direct measurement for membrane bound and intracellular urokinase per cell. The screening process can incorporate the other measurements used in the method for evaluating the presence of metastatic activity. The presence of urokinase receptors, plasminogen activator inhibitors, tumor growth factors and membrane associated hormone receptors also can be measured.

Heretofore, the mean urokinase content of tissue extracts or culture supernatants generally measured as compared to total protein has been examined to indicate potential for metastatic decrease or tumor recurrence. The unique measurement and correlation of urokinase content to DNA content of the same cells or same sample can give a quantitative indication of metastatic activity of the tumor, which indicates immediate concerns about the spread of the cancer from the primary tumor and therefore more aggressive post-operative treatments. No previous method has been developed to accurately measure the intracellular urokinase content, membrane-bound urokinase and cellular secretion levels and then correlate those urokinase levels with DNA content, DNA synthesis, and other markers of aggressive tumor growth to determine the metastatic potential in an individual patient.

DETAILED DESCRIPTION OF THE METHOD

Figure 1A:
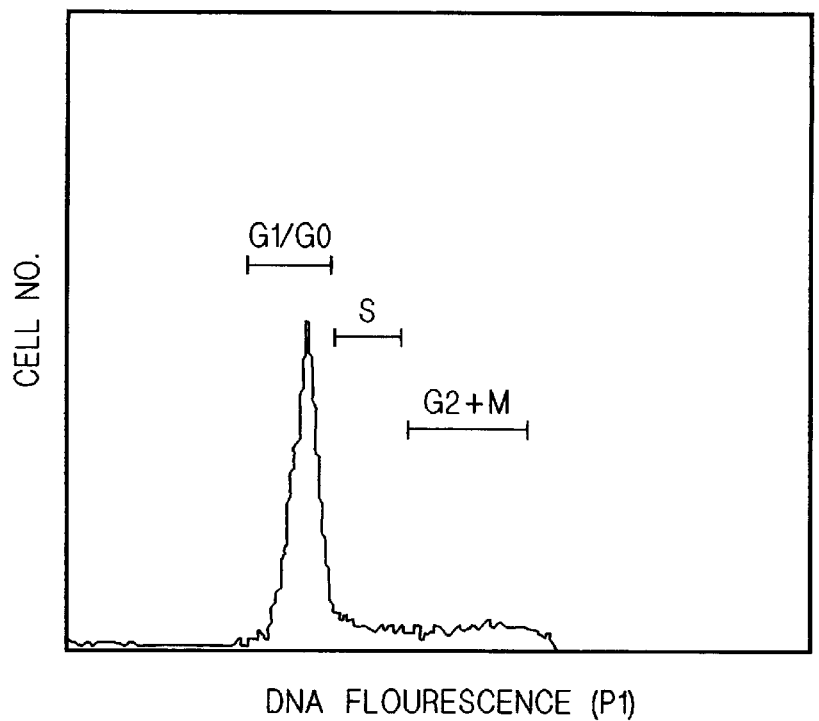
FIG. 1A is a graphic representation of DNA found in CS glioma cells, measured by fluorescent flow cytometry, which shows the DNA content relative to the stage of the cell cycle.

The method for analysis of the metastatic potential of cells can be used for diagnostic, research, or any other purpose. It is not the intent to limit the type of cell that can be isolated and evaluated nor to limit the type of histological tissue that can be labeled with the fluorescent anti-urokinase antibodies for measuring the urokinase in situ in the tissue biopsy. The following is a general description of the method including the preferred method. It is not intended to disclose every mode to practice the invention, and substitutions and modifications to the steps described herein may be made without departing from the scope of the invention.

Antibodies can be formed against the two major molecular forms of uPA using established methods of isolating the HMW-uPA or LMW-uPA urokinase protein then immunizing animals to produce the antibodies. Typically, the uPA antigen is isolated from human urine or cell culture medium by absorption chromatography. Most commercial anti-uPA antibodies are murine antibodies made against human urokinase. The commercial antibodies (such as AD#394 and AD#3689 American Diagnostica, Inc.) can detect the 54 kDA HMW-uPA or the 33 KDa LMW-uPA forms of uPA, but they cannot distinguish between the 54 kDA HMW-uPA active and proenzyme scuPA molecular forms (also 54 kDA). The HMW-uPA is used by the tumor cells to rapidly invade adjacent tissue. Therefore, it is important to distinguish between HMW-uPA with its proenzyme scuPA and LMW-uPA. The commercial anti-uPA antibodies can inhibit the normal enzymatic activation of plasminogen to plasmin.

Presently, none of the commercial anti-uPA antibodies are specific for detection of the actual cleavage sites where activation of the proenzyme (scuPA) occurs. Plasmin converts scuPA to HMW-uPA. Measurements of scuPA may be performed by preincubation of duplicate samples with and without plasmin and measuring the presence of HMW-uPA in both samples and quantifying the difference attributable to scuPA.

Anti-uPA antibodies can be used as the primary anti-body in sandwich assays or in permeabilized cytology preparations, wherein either the anti-uPA antibodies can be fluorescently labeled or a secondary, fluorescent labeled, antibody can be attached to the anti-uPA primary antibody; thus permitting fluorescence image analysis or laser activated flow cytometry analysis to determine the amount of the intracellular and membrane bound urokinase in each cell. Also the anti-uPA antibodies themselves can be conjugated with markers having detectable physical or chemical properties. The markers are well known in the field of immunoassays. The preferred method utilizes markers with detectable light emissions by fluorescence, phosphorescence or luminescence, however, markers that absorb light, such as peroxidase, and radioactive labels can also be used. Primary and secondary detection of the antibodies may be useful in the invention with different types of cell or tissue samples The cells to be examined are first isolated. The cells may be from a tumor, fine-needle biopsy or cytological sample. The anti-uPA antibodies are incubated with the cells. In a preferred method for examination of intracellular and membrane-bound extracellular urokinase, the cells are labeled with fluorescent markers for digital image analysis. Using digital image analysis the anti-uPA antibodies can be located and quantitatively measured in both the cytoplasm and where the urokinase is bound to the cell membrane. These measurements are used statistically to give the relative distribution and absolute concentrations of membrane-bound and cytoplasmic urokinase in biopsy cells. This data can then be used to statistically compare the urokinase levels and distribution in those cells with tumor cells from other patients, thus giving a quantitative benchmark as to the metastatic state of those tumors in each individual patient. This data also can be used in retrospective studies where the time to reoccurrence, degree of metastasis and morbidity are known. Cumulative data on patients can then be used to provide a prognostic indicator of the degree of active metastasis in primary tumors.

Another alternative method for analysis of cellular urokinase is by flow cytometry. The membrane-bound urokinase can be measured directly by incubating the cells with the fluorescent labeled antibodies against the different molecular forms of urokinase. Whereas, the intracellular urokinase can only be measured after the cell wall has been partially permeated by chemical or electrochemical poration techniques. Then the anti-uPA antibodies can penetrate the cell and attach to the urokinase in the cytoplasm. Laser activated flow cytometry can be used to determine uPA content per cell. The cells containing uPA can be sorted as they pass through the flow cytometer and selected for uPA content. The selected cells are further examined by digital image analysis for cytoplasmic or intracellular uPA and extracellular, membrane bound uPA. A large population of cells can be examined using flow cytometry and fluorescent antibodies as a screening method prior to digital image analysis.

An alternate preferred method involves the parallel measurement of membrane bound urokinase, intracellular (cytoplasmic) urokinase levels using digital image analysis of the fluorescent micrographs and correlations with DNA content and DNA synthesis rates as measured by flow cytometry or image analysis. Abnormal DNA levels are related to the aggressive growth of the tumor cells.

If the cells are not actively metastasizing they have no urokinase or very low levels of urokinase including low amounts of membrane-bound urokinase and high levels of Plasminogen Activator Inhibitor (PAI-1 and/or PAI-2). These are characteristic of non-invading, non-metastasizing primary tumors or metastatic tumor cells that already are well established at the metastatic site. The tumor cells that are actively invading adjacent tissues and metastasizing are characterized by high levels of membrane-bound HMW-uPA or scuPA type urokinase, abnormal levels of DNA and low levels of PAI-1. The quantitative measurements of DNA, urokinase and PAI-1 enable precise comparisons to establish the unique metabolic state of the tumor cells that are preparing for or actively metastasizing.

The method of this invention also includes the step of measuring the DNA content in the cells isolated from patient biopsies. The nuclear DNA content can be determined by labelling with vital stains such as propidium iodide (PI), Hoeschst stain, DAPI or by antibodies reactive to DNA or a DNA precursor as described in U.S. Pat. No. 4,780,406, issued Oct. 25, 1988, to Dolbeare and Gray which has been incorporated by reference herein. Urokinase expression and secretion is regulated by certain cytokines and hormones. It has been shown that the recurrence of breast and other cancers is related to the number of estrogen (ER) and progesterone receptors (PgR) found on the surface of the tumor cells. The use of fluorescent antibodies against ER and PgR enables the simultaneous measurement of receptor density on the cell surface to be compared with the DNA and the urokinase levels in normal and tumor cells. The hormone receptor levels can be measured either by flow cytometry or digital image analysis and then directly compared with the urokinase levels. The DNA content is preferably measured using flow cytometry, but also can be measured by image cytometry.

By using different fluorescent labels or markers that can be measured at essentially the same time at two or more different wavelengths the same cell population that is examined for urokinase can be simultaneously assayed for PAI, DNA content, DNA synthesis rate or hormone receptors. For example, fluorescent antibodies to both the DNA or DNA precursors and urokinase forms can be used with different emission characteristics, thus the flow cytometer can simultaneously measure two or more color fluorescence of the two or more antibodies. Digital image capture also can be performed at multiple wavelengths thus enabling measurements of more than one intracellular protein or membrane receptor and DNA in the same tissue specimens.

Digital analysis measurement of the amount of urokinase, in the cytoplasm or membrane-bound, also can be used with the measurement of DNA content by flow cytometry. The identical cell population is not necessarily used for each analysis, however, since aliquot samples are used from the same cells that were isolated from the surgical biopsy.

Another alternative method also measures the synthesis rate of DNA in the cells by pulse labeling with DNA precursor amino acids (BdUR or IdUR) and then labeling with fluorescent antibodies against the DNA precursor to determine the amount of incorporation per unit time. (Gratzner, H. G. and Leif, R. C. "An immunofluorescence method for monitoring DNA synthesis by flow cytometry." Cytometry 6: 385–389, 1983.). The DNA synthesis rate can either be measured by flow cytometry or fluorescence image analysis and thus compared directly to the levels of urokinase in the tumor cells.

Another alternative method is measurement of urokinase using fluorescence image analysis of de-paraffinized or frozen histology sections from biopsy tissues. DNA can be measured simultaneously using a vital fluorescent stain (PI or DAPI) or fluorescent labeled antibodies against BdUR or IdUR that emits fluorescence at a different wavelength than does the labeled anti-uPA antibodies. Supporting flow cytometry data can be obtained from thick sections from the tumor specimens, whereupon the cells are dissociated, treated with RNAse, the nuclei freed from the cytoplasm and flow cytometry performed on the nuclei. This data is then compared to the urokinase levels or image analysis data on cells taken from the same biopsy tissue.

To illustrate the method of this invention the correlation of urokinase on a cell by cell basis and DNA content have been examined in two glioma cell lines obtained from surgical biopsies removed from two different patients (CS and HBR09) with brain tumors. Comparisons were made among: 1) autofluorescence measured in cells treated with a non-specific immunoglobin (IgG) as controls, 2) green fluorescence measured from cells treated with FITC-labeled antibodies against urokinase, and 3) red fluorescence measured from the DNA in the same cells stained with propidium iodide, using cell samples that were disassociated for flow cytometry. The CS cells are less invasive and metastatic brain tumor cells than HBR09 cells.

Figure 1B:
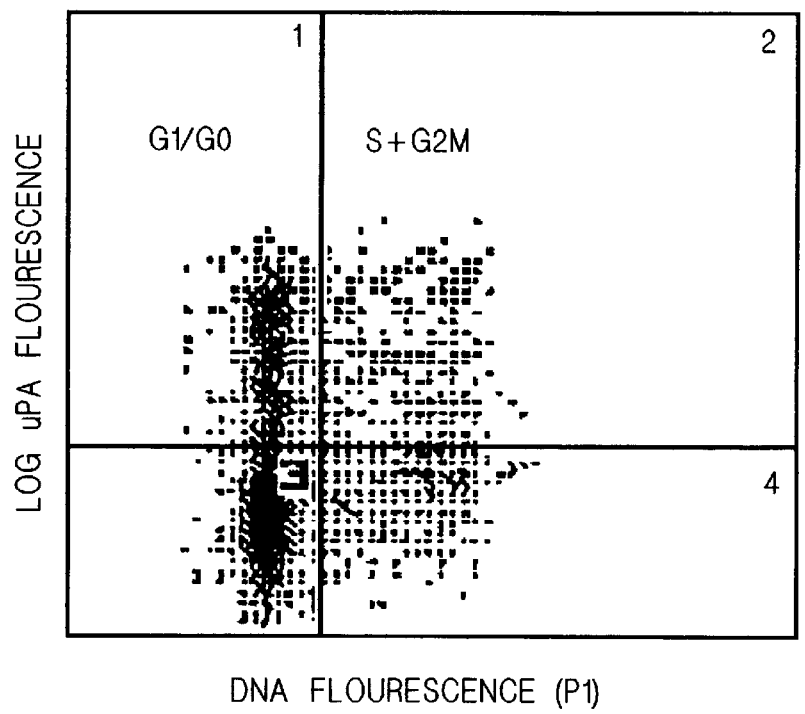
FIG. 1B is a two dimensional plot of the log fluorescence from urokinase (ordinate) vs. the log fluorescence from the DNA contained in the CS glioma cells, as measured by flow cytometry.
Figure 2A:
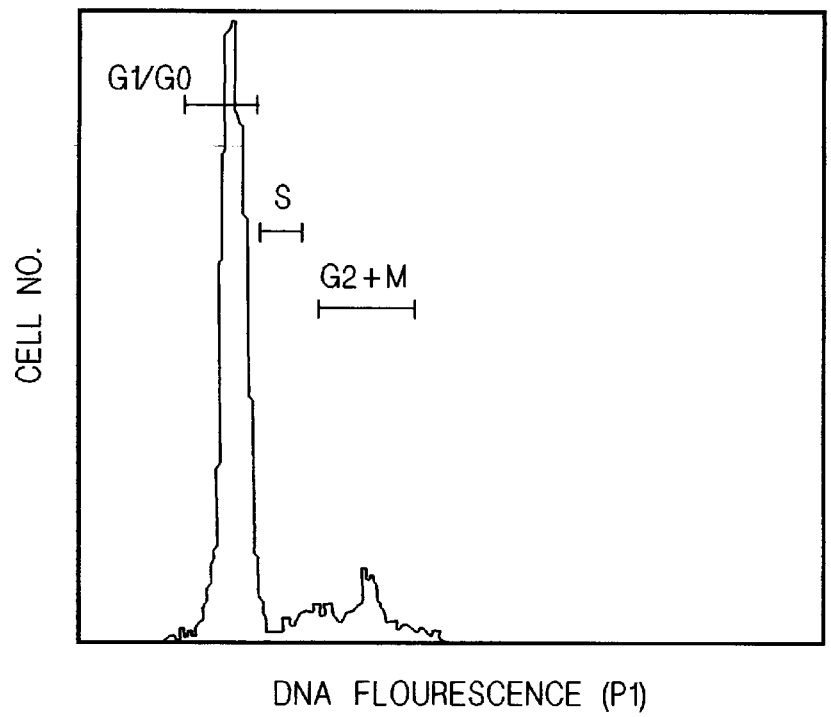
FIG. 2A is a graphic representation of DNA found in HBR09 glioma cells, measured by fluorescent flow cytometry, which shows the DNA content relative to the stage of the cell cycle.
Figure 2B:
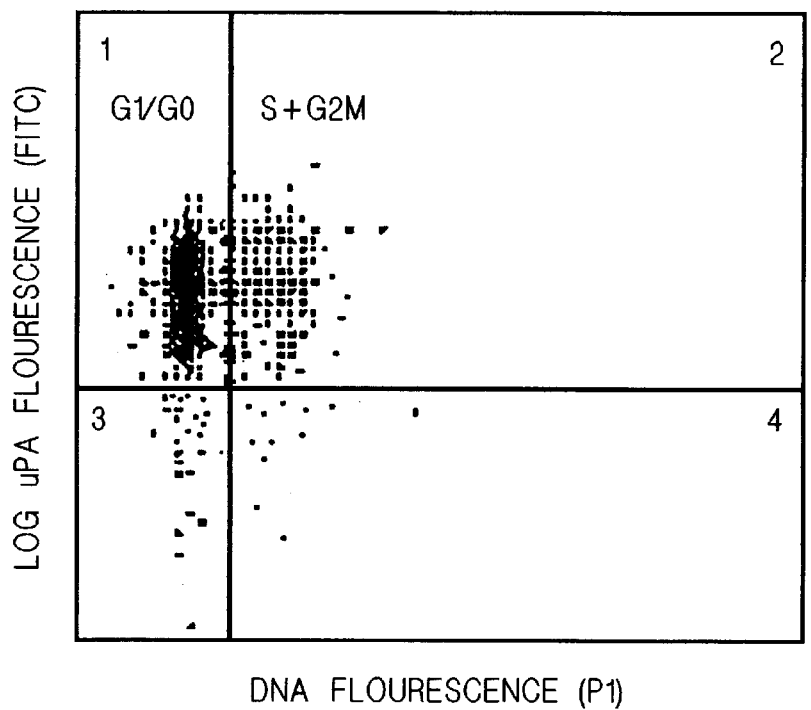
FIG. 2B is a two dimensional plot of the log fluorescence from urokinase (ordinate) vs. the log fluorescence from the DNA contained in the HBR09 glioma cells, as measured by flow cytometry.

The DNA was measured by flow cytometry for the CS cells and HBR09 cells and FIGS. 1A and 2A show the DNA content for each cell type in various stages of the cell cycle. The same cells were measured by flow cytometry for HMW-UPA (with commercial anti-uPA antibodies HMW-uPA that cannot distinguish between scuPA and active HMW-UPA). FIG. 1B illustrates the correlation of the uPA content vs. the DNA content in the CS cells, while FIG. 2B illustrates a different pattern of uPA content vs. the DNA content in the more invasive HBR09 cells. Table 1 summarizes the presence of DNA and uPA in the CS and HBR09 tumor cell lines. It should be noted that the difference in uPA content between the CS and HBR09 cell types is more pronounced when the cells are in the resting cells (G1/G0) compared to the those cells that are active synthesizing DNA and dividing (S & $G_{2+M}$). In other tumor cells the difference may be greater in S and $G_{2+M}$ phases.

TABLE 1

SIMULTANEOUS FLOW CYTOMETRY MEASUREMENT OF DNA AND uPA
IN HUMAN BRAIN TUMOR CELLS
Mean Fluorescence Levels - (DNA) PI and uPA (FITC-anti-uPA MAb)

| PHASE (CELL CYCLE) | G1/Go | | | | | S + G2M | | | | |
|---|---|---|---|---|---|---|---|---|---|---|
| CELL I.D. | % Cells | DNA | S.D. | uPA | S.D. | % Cells | DNA | S.D. | uPA | S.D. |
| IgG (Control) | 78.8 | 16.7 | 2.00 | 0.74 | 0.15 | 0.6 | 29 | 3.60 | 2.18 | 0.11 |
| CS | 77.3 | 17.2 | 1.50 | 1.90 | 0.21 | 7 | 29.1 | 0.41 | 4.74 | 0.24 |
| HBR09 | 82.6 | 9.9 | 1.00 | 12.22 | 0.17 | 15 | 17.4 | 2.20 | 15.48 | 0.18 |
| | RATIO of uPA HBR09/CS = 6.43 | | | | | RATIO OF uPA HBR09/CS = 3.27 | | | | |

Table 1 is a summary of simultaneous flow cytometry measurements using fluorescent markers for DNA and uPA in IgG-treated control cells; CS cells (illustrative of a less invasive glioma tumor); and HBR09 cells from a more invasive tumor. DNA values are based on the mean fluorescence from propidium iodide (PI) stain while uPA values are based on FITC-labeled, anti-uPA antibodies that bind to HMW-UPA and scuPA. The DNA and uPA values for the IgG controls are mean measurements of the non-specific autofluorescence measured from the cells in the PI and FITC bandpass regions, respectively. The control cells had very little uPA, especially in the resting phase (G1/G0). The CS cells in $G_1/G_0$ contain 1.7 times more DNA than the HBR09 cells, but the HBR09 cells contain 6.4 times more UPA. The same relationship is present in the S+$G_{2+M}$ phases, however, the HBR09 cells contain only 3.3 times more uPA than do the CS cells.

FIGS. 1A and 2A are graphic representations of the cell distribution data for DNA content, obtained from the flow cytometer printouts and summarized in Table 1. The legends show the relative distribution of the cells in the $G_1/G_0$, S, and $G_{2+M}$ phases of the cell cycle. FIG. 1A is a semilog plot of the CS cell number vs. the DNA content, where the DNA is represented by the log fluorescence from PI staining (abscissa). FIG. 2A is a semi-log plot of the cell number vs. the DNA content for the HBR09 cells.

FIGS. 1B and 2B are graphic representations of the uPA and DNA content for the CS cells and HBR09 cells, respectively, measured by two-color flow cytometry as summarized in Table 1. DNA was measured by the DNA specific fluorescent dye propidium iodide and uPA was measured by FITC-labeled anti-urokinase antibodies. In FIGS. 1A and 2A zone 1 is the fluorescence measurement for the DNA content in the cells at $G_1/G_0$, zone 2 is for the cells in S+$G_{2+M}$, and zones 3 and 4 represent low-level background /autofluorescence levels below the gating value selected from identical runs with negative controls. In general, the DNA fluorescence for the HBR09 cells in the S and $G_{2+M}$ phase (FIG. 2B, zone 2) is higher than the CS cells (FIG. 1B, zone 2). Furthermore, the distribution of HBR09 cells containing high levels of uPA in the resting phase (FIG. 1B, zone 1) is more focused than the CS cells (FIG. 2B, zone 1.) Eighty-eight percent of the HBR09 cells in the resting phase and 96% of the cells in S and $G_{2+M}$ (zone 2) have high levels urokinase in contrast to the CS cells where 42% in the resting phase and only 54% of the cells in S and $G_{2+M}$ have significant levels of urokinase. Also the mean content of uPA per HBR09 cell is greater than the CS cells in all phases of the cell cycle.

Flow cytometry can be used for disassociated cell samples to initially screen for the abnormal DNA content and uPA profile indicating aggressive tumors. Cells with abnormal DNA and high levels of uPA particularly in the S phase merit attention for potentially aggressive tumor tissue and further examination by digital image analysis. However, the analysis by flow cytometry using this method may be sufficient with existing pathological procedures and tests to make a determination on treatment of a dangerously malignant tumor.

Image analysis was performed on fluorescent uPA antibodies in CS and HBR09 cells. Image analysis can quantify the presence of uPA by measuring the fluorescence emitted by labeled antibodies that are bound directly to uPA. Table 2 illustrates the comparison of flow cytometry analysis and digital image analysis of fluorescent-labeled uPA antibodies, wherein each sample of glioma cells were split into two groups for parallel assays of uPA. Table 2 shows the high levels of uPA in CS and HBR09. However, in-comparison HBR09 has much higher levels of uPA than CS as confirmed by both flow cytometry and image analysis. Note that the image analysis method show a greater ratio of UPA in the HBR09 cells as compared to the CS cells and that the standard deviation of the mean fluorescence is smaller (8–9%) compared to the flow cytometry data (10–35%) on the same cells.

TABLE 2

COMPARISON OF UROKINASE IN CONTROL AND BRAIN CANCER CELLS USING FLUORESCENT-LABELED uPA ANTIBODIES

| | CELL LINE | MEAN FLUORES-CENCE | S.D. | MEMBRANE-BOUND uPA | S.D. |
|---|---|---|---|---|---|
| FLOW CYTO-METRY | IgG (Control) | 2.05 | 0.3 | — | |
| | CS | 6.13 | 0.1 | — | |
| | HBR09 | 32.25 | 11.3 | | |
| | RATIO HBR09/CS = 5.26/1* | | | | |
| IMAGE ANAL-YSIS | IgG (Control) | 1.86 | 0.1 | — | |
| | CS | 11.3 | 0.76 (8%) | 78.3 | 3.41 (4%) |
| | HBR09 | 74.1 | 6.34 (9%) | 821.9 | 47.8 (6%) |
| | RATIO HBR09/CS = 7.56/1 | | | HBR09/CS = 10.5/1 | |

*RATIO HBR09/CS = 7.4 after autofluorescence is subtracted

Image analysis has the further benefit of measuring the membrane bound uPA. Using the method of this invention, a determination of the presence of membrane bound uPA is made when indicated. The fluorescent microscope can be focused on different levels within each cell before the images are digitized, thus it can be distinguished if the uPA is on the cell surface or within the cell cytoplasm. Digital levels can also be selected so that areas of the cell surface or cytoplasm emitting a given fluorescence intensity can be measured and labeled, thus providing quantitative data and a visual reference for use with other cytopathological evaluations. The presence of uPA at the membrane indicates a tumor cell that is actively invading adjacent tissues or migrating to a remote site to establish a new metastatic tumor. In Table 2 the membrane bound uPA is significantly higher in the more invasive HBR09 than in the CS cells. The use of image analysis is precise and can be used on tissue such as biopsies on slides in which the cells have not been disassociated. Image analysis can also be used to quantify they different forms of urokinase in the same cells by using different fluorescent antibodies for different forms of urokinase.

The method also includes screening for the presence of plasminogen activation inhibitors (PAI) PAI-1 and PAI-2. Antibodies specific to PAI-1 and PAI-2 with a fluorescent label may be used. An aggressive tumor will have higher levels of abnormal DNA (tetraploid or greater) while metastatic cells will have low levels of PAI-1 or PAI-2 and high levels of uPA.

Membrane bound PAI-1 and PAI-2 measurements can also be very important since the PAI can compete with the uPA for binding to the uPA receptor on the tumor cell surface. The method can also incorporate fluorescent antibodies specific for the uPA receptors on the cell surface. Comparison of the DNA content, DNA synthesis rate, uPA content, membrane-bound uPA, PAI and uPA receptor density in tumor cells can give the clinician much clearer insight into the metastatic potential of each tumor that is biopsied. The combined method of cytology testing described herein is required to provide a systematic way of acquiring the required data and accuracy needed for determining the true metastatic potential of a particular tumor. This information can provide the basis for custom therapeutic regimens that are designed for each cancer patient's circumstance at the time of the biopsy.

The examples and methods described herein exemplify the invention and are not intended to limit the scope of the invention in any way. Other methods of practicing the invention will be apparent to those skilled in the art.

I claim:

1. A method of measuring metastatic activity by direct quantitative detection of urokinase and DNA for use in the evaluation of the presence of tumor cells with invasive characteristics comprising the steps of (a) selecting the cells to be examined;

(b) incubating a sample of the cells with antibodies specific to urokinase and a label specific to DNA;

(c) measuring directly the antibodies specific for the amounts of urokinase present in the sample on a cell by cell basis;

(d) measuring the DNA content simultaneously as step (c) in the same sample of the cells isolated in step (a) on a cell by cell basis; and (e) identifying the cell populations in the sample on a cell by cell basis for DNA aneuploidy and high urokinase amounts; and (f) further evaluating the cell populations identified in step (e) for DNA content for resting cells (G1/G0) and synthesizing and dividing cells (S and G2+M); and (g) correlating DNA content for resting cells (G1/G0) and synthesizing and dividing cells (S and $G_{2+m}$) with high urokinase levels to identify tumor cells with more invasive characteristics which have lower DNA content and higher urokinase content as compared to the high DNA content and low urokinase content of tumor cells with less invasive characteristics in the resting phase (G1/G0).

2. A method of measuring metastatic activity by direct quantitative detection of urokinase and DNA of claim 1 wherein the urokinase antibodies are specific to the group selected from scuPA and HMW-uPA or mixtures thereof.

3. A method of measuring metastatic activity by direct quantitative detection of urokinase and DNA of claim 1 wherein steps (c) and (d) the simultaneous measurements are performed by analytical cytometry and the antibodies specific to urokinase and the label specific to DNA have a marker detectable by analytical cytometry techniques.

4. A method of measuring metastatic activity by direct quantitative detection of urokinase and DNA of claim 1 wherein the antibodies specific to urokinase are monoclonal antibodies.

5. A method of measuring metastatic activity by direct quantitative detection of urokinase and DNA of claim 1 wherein the antibodies specific to urokinase are polyclonal antibodies.

6. A method of measuring metastatic activity by direct quantitative detection of urokinase and DNA of claim 1 wherein the antibodies specific to urokinase have a fluorescent marker.

7. A method of measuring metastatic activity by direct quantitative detection of urokinase and DNA of claim 1 comprising the additional step of measuring DNA synthesis by analytical flow cytometry performed on the same cell sample simultaneously with the DNA content measured in step (d).

8. A method of measuring metastatic activity by direct quantitative detection of urokinase and DNA of claim 1 comprising the additional steps of incubating a sample of the cells with plasminogen activator inhibitor antibodies and measuring quantitatively the presence of bound plasminogen activator inhibitor antibodies by digital image analysis and correlating the plasminogen activator inhibitor content to the urokinase content identifying the more metastatic cells that have comparably low levels of plasminogen activator inhibitor content and high levels of urokinase content.

9. A method of measuring metastatic activity by direct quantitative detection of urokinase and DNA of claim 1 comprising the additional steps of incubating a sample of the cells with antibodies against plasminogen activator inhibitors and measuring quantitatively the presence of plasminogen activator inhibitor bound antibodies by flow cytometry and correlating the plasminogen activator inhibitor content to the urokinase content identifying the more metastatic cells that have comparably low levels of plasminogen activator inhibitor content and high levels of urokinase content.

10. A method of measuring potential metastatic activity by direct quantitative detection of urokinase and DNA of claim 1 comprising the additional steps of selecting cells with membrane-bound urokinase, incubating a sample of the cells with urokinase receptor markers and measuring quantitatively the urokinase receptor density and further correlating these cells with high urokinase receptor density for those cells with high urokinase content and low plasminogen activator inhibitor content which are characteristic of high invasiveness.

11. A method of measuring metastatic activity by direct quantitative detection of urokinase and DNA of claim 1 wherein the label specific to DNA is a measurable marker.

12. A method of measuring metastatic activity by direct quantitative detection of urokinase and DNA for use in the evaluation of the presence of metastatic activity in tumor cells comprising the steps of
   (a) selecting the cells to be examined;
   (b) incubating a sample of the cells with antibodies specific to urokinase and a label specific to DNA;
   (c) measuring directly the antibodies specific for the amounts of urokinase present in the sample on a cell by cell basis using flow cytometry;
   (d) simultaneously as step (c) measuring directly the DNA content of the cells isolated in step (a) on a cell by cell basis;
   (e) identifying and isolating the cell populations in the sample on a cell by cell basis with DNA aneuploidy and high urokinase levels; and
   (f) measuring the intracellular and membrane bound urokinase using digital image analysis of individual cells in the cell population identified and isolated in step (e);
   (g) simultaneously with step (f), using digital image analysis of individual cells for the cell populations identified and isolated in step (e), measuring DNA content for resting cells (G1/G0) and synthesizing and dividing cells (S and $G_{2+m}$); and
   (h) correlating DNA content for resting cells (G1/G0) and synthesizing and dividing cells (S and $G_{2+m}$) which have lower DNA content as compared to the high DNA content of tumor cells with less invasive characteristics at the resting phase (G1/G0) with high intracellular and high membrane bound urokinase to identify tumor cells with more invasive characteristics which have high membrane bound urokinase as compared to tumor cells with less invasive characteristics.

13. A method of measuring metastatic activity by quantitative detection of urokinase and DNA of claim 12 comprising the additional measurement DNA synthesis rate in a sample of the cells identified and isolated in step (e) and further correlating the DNA synthesis rate of cells with higher urokinase content whereby metastatic cells have a lower DNA synthesis rate than non-metastatic cells.

14. A method of measuring metastatic activity by direct quantitative detection of urokinase and DNA of claim 12 wherein the antibodies specific to urokinase are monoclonal antibodies.

15. A method of measuring metastatic activity by direct quantitative detection of urokinase and DNA of claim 12 wherein the antibodies specific to urokinase are polyclonal antibodies.

16. A method of measuring metastatic activity by direct quantitative detection of urokinase and DNA of claim 12 wherein the antibodies specific to urokinase have a detectable light emitting marker.

17. A method of measuring metastatic activity by direct quantitative detection of urokinase and DNA of claim 12 wherein the label specific to DNA has a detectable light emitting marker.

18. A method of measuring metastatic activity by direct quantitative detection of urokinase and DNA of claim 12 comprising the additional steps of incubating a sample of the cells with plasminogen activator inhibitor antibodies and measuring quantitatively the presence of bound plasminogen activator inhibitor antibodies by digital image analysis and correlating the plasminogen activator inhibitor content to the urokinase content identifying the more metastatic cells that have comparably low levels of plasminogen activator inhibitor content and high levels of urokinase content.

19. A method of measuring metastatic activity by direct quantitative detection of urokinase and DNA of claim 12 comprising the additional steps of incubating a sample of the cells with antibodies against plasminogen activator inhibitors and measuring quantitatively the presence of plasminogen activator inhibitor bound antibodies by flow cytometry and correlating the plasminogen activator inhibitor content to the urokinase content identifying the more metastatic cells that have comparably low levels of plasminogen activator inhibitor content and high levels of urokinase content.

20. A method of measuring metastatic activity by direct quantitative detection of urokinase and DNA of claim 12 comprising the additional steps of incubating a sample of the cells with urokinase receptor markers and measuring quantitatively the urokinase receptor density and further correlating those cells with high urokinase receptor density with those cells with high urokinase content and low plasminogen activator inhibitor content which are characteristic of high invasiveness.

21. The method of measuring metastatic activity by direct quantitative detection of urokinase and DNA of claim 12 wherein the urokinase antibodies are specific to the group consisting of scuPA, LMW-UPA and HMW-UPA or mixtures thereof.

* * * * *